(12) United States Patent
Almarode

(10) Patent No.: US 11,654,120 B2
(45) Date of Patent: May 23, 2023

(54) COMPOSITION FOR TREATING SKIN CONDITIONS

(71) Applicant: OLLIE'S HEALTH, LLC, Pasco, WA (US)

(72) Inventor: Marshall Ollie Almarode, Pasco, WA (US)

(73) Assignee: OLLIE'S HEALTH, LLC, Pasco, WA (US)

( * ) Notice: Subject to any disclaimer, the term of this patent is extended or adjusted under 35 U.S.C. 154(b) by 0 days.

(21) Appl. No.: 16/324,265

(22) PCT Filed: Aug. 10, 2017

(86) PCT No.: PCT/US2017/046311
§ 371 (c)(1),
(2) Date: Feb. 8, 2019

(87) PCT Pub. No.: WO2018/031783
PCT Pub. Date: Feb. 15, 2018

(65) Prior Publication Data
US 2019/0183814 A1    Jun. 20, 2019

Related U.S. Application Data

(60) Provisional application No. 62/373,921, filed on Aug. 11, 2016.

(51) Int. Cl.
| | | |
|---|---|---|
| *A61K 31/122* | (2006.01) | |
| *A61K 36/11* | (2006.01) | |
| *A61K 31/355* | (2006.01) | |
| *A61K 31/375* | (2006.01) | |
| *A61K 31/728* | (2006.01) | |
| *A61K 36/05* | (2006.01) | |
| *A61Q 19/08* | (2006.01) | |
| *A61K 8/9789* | (2017.01) | |
| *A61K 8/35* | (2006.01) | |
| *A61Q 19/00* | (2006.01) | |
| *A61K 8/9741* | (2017.01) | |
| *A61K 31/4188* | (2006.01) | |
| *A61K 31/7048* | (2006.01) | |
| *A61K 36/15* | (2006.01) | |
| *A61K 36/74* | (2006.01) | |
| *A61K 38/39* | (2006.01) | |
| *A61K 9/00* | (2006.01) | |
| *A61P 17/02* | (2006.01) | |
| *A61Q 17/04* | (2006.01) | |

(52) U.S. Cl.
CPC .............. *A61K 31/122* (2013.01); *A61K 8/35* (2013.01); *A61K 8/9741* (2017.08); *A61K 8/9789* (2017.08); *A61K 9/0014* (2013.01); *A61K 31/355* (2013.01); *A61K 31/375* (2013.01); *A61K 31/4188* (2013.01); *A61K 31/7048* (2013.01); *A61K 31/728* (2013.01); *A61K 36/05* (2013.01); *A61K 36/11* (2013.01); *A61K 36/15* (2013.01); *A61K 36/74* (2013.01); *A61K 38/39* (2013.01); *A61P 17/02* (2018.01); *A61Q 17/04* (2013.01); *A61Q 19/00* (2013.01); *A61Q 19/004* (2013.01); *A61Q 19/08* (2013.01); *A61K 2800/522* (2013.01); *A61K 2800/92* (2013.01)

(58) Field of Classification Search
CPC ... A61K 31/122; A61K 8/9741; A61K 8/9789
See application file for complete search history.

(56) References Cited

U.S. PATENT DOCUMENTS

| | | |
|---|---|---|
| 2002/0127256 A1 | 9/2002 | Murad |
| 2008/0014156 A1 | 1/2008 | Horn |
| 2008/0241101 A1 | 10/2008 | Amano et al. |
| 2009/0263367 A1 | 10/2009 | Foley |
| 2012/0141387 A1 | 6/2012 | Msika et al. |
| 2016/0151306 A1 | 6/2016 | Minatelli et al. |

FOREIGN PATENT DOCUMENTS

| | | | | |
|---|---|---|---|---|
| CN | 101554363 A | * | 10/2009 | |
| FR | 2942720 A1 | * | 9/2010 | ............... A61K 8/02 |
| JP | 2010088403 A | * | 4/2010 | |

OTHER PUBLICATIONS

Neutraceuticals World: Suntegrity Sun Care. Internet archive: Dec. 20, 2011. Retrieved from the Internet on: Apr. 27, 2020. Retrieved from the Internet:: <URL: https://web.archive.org/web/20111210032059/ https://www.nutraceuticalsworld.com/issues/2010-11/view_products/ suntegrity-sun-care/>. (Year: 2011).*
Ambati et al. Mar. Drugs, Dec. 2014, 128-152 (Year: 2014).*
Amazon Skin-P Support. From "RainTree Nutrition: Amazon Support". Internet archive date: 2004-. Retrieved from the Interne on Sep. 21, 2020. Retrieved from: <URL: https://web.archive.org/web/ 20040129000553/https://rain-tree.com/amazon-skin-p-support. htm>. (Year: 2006).*
Mammone et al. Phytother. Res. 20, (2006) 178-183 (Year: 2006).*
MWW Group. Study demonstrates the anti-inflammatory properties of pine bark extract. Web publication date: Jul. 14, 2009. Retrieved from the Internet: <URL: https://www.eurekalert.org/pub_releases/ 2009-07/mg-sdt071409.php>. (Year: 2009).*
International Search Report and Written Opinion in International Application No. PCT/US2017/046311, dated Nov. 28, 2017.

* cited by examiner

*Primary Examiner* — Amy L Clark
(74) *Attorney, Agent, or Firm* — Raphael Bellum PLLC

(57) ABSTRACT

This disclosure relates to new compositions and methods for treating skin conditions as a result of sun damage. In one embodiment this disclosure pertains to new compositions for treating or preventing sunburns, skin damage, and/or harm from radiation, such as UV radiation.

13 Claims, No Drawings

COMPOSITION FOR TREATING SKIN CONDITIONS

CROSS REFERENCE TO OTHER RELATED APPLICATIONS

This application claims priority to U.S. Provisional Application Ser. No. 62/373,921 filed on Aug. 11, 2016, which is hereby incorporated in its entirety.

TECHNICAL FIELD

This disclosure relates to the skin care industry. In particular, this disclosure relates to compositions and methods of treatment for skin conditions, e.g., sunburns.

BACKGROUND

The skin is the largest organ of the human body and is subjected to the harshest conditions because of exposure to the elements. It is next to impossible, and impractical, to cover the entire body to fight off the elements. One of the biggest threats to overall skin health is the sun.

Sunlight, in the form of Ultraviolet B (UVB), is needed for developing Vitamin D, which helps with the body absorbing and utilizing calcium. In fact, a number of people do not get enough sunlight leading to a Vitamin D deficiency and thus a calcium deficiency and osteomalacia. However, the sun also has serious adverse effects on the skin and human body. Sunburns, skin cancer, and melanoma can result from overexposure of radiation from the sun. In particular Ultraviolet (UV) radiation. In response many treatments and products have become available to block sun radiation and protect the skin.

These products usually take the form of topical applications like sunscreens or lotions which are troublesome for a number of reasons. Topical solutions are usually difficult to apply to all exposed areas, e.g., the back. Topical solutions also cause skin irritation, have unsatisfactory consistency, e.g., too wet or oily, and/or contain toxic ingredients. These adverse factors cause people to avoid these treatments or products.

In addition, there are few products that effectively cure sunburns as opposed to being just a preventive measure. Many people rely on home remedies, e.g., applying household items like dairy products or cold showers, for relieving pain as opposed to actually curing the sunburn. Leading to many inconsistent results, wasted time and effort.

There exists a need for a readily available product for not only relieving sunburn pain but curing the sunburn as well. There also exists a need for an oral application for ease and convenience but for health purposes as well. As well as need for an internal treatment versus an external treatment.

DETAILED DESCRIPTION

Disclosed herein are newly developed compositions and methods for treating skin conditions. In one embodiment, the compositions disclosed herein comprise 4-hydroxycinnamic acid, 3 methoxy-4-hydroxycinnamic acid, 3,4-dihydroxycinnamic acid, 3-methoxy-4-hydroxybenzoic acid, or 3-caffeoilquinic acid.

Disclosed herein are new methods of administering treatment for skin conditions. In one embodiment, the skin condition is skin cancer. In one embodiment, the skin condition is a sunburn. In one embodiment, the method of treatment comprises a method of prevention.

Disclosed herein is a composition comprising Astaxanthin and Polypodium Leucotomos extract. In one embodiment, the composition comprises Hyaluronic Acid, Cat's Claw extract, Collagen type II, Hesperidin, Horse tail extract, Pine bark extract, biotin, Vitamin C, or Vitamin E.

As used herein, the term "Astaxanthin" refers to a compound with the following structural formula:

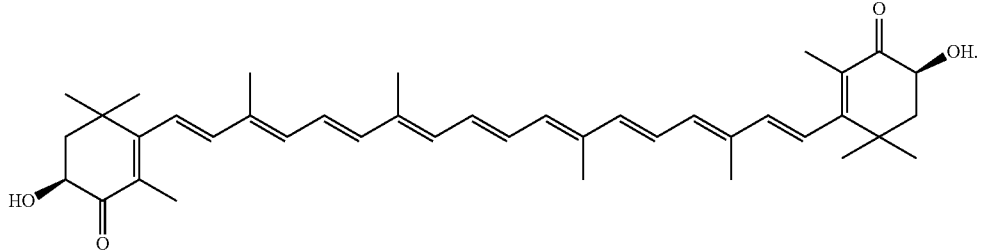 [SMILES: CC1=C(/C=C/C(C)=C/C=C/C(C)=C/C=C/C=C(C)/C=C/C=C(C)/C=C/C2=C(C)C(=O)[C@@H](O)CC2(C)C)C(C)(C)C[C@H](O)C1=O]

In one embodiment, Astaxanthin is from an extract of Haematococcus pluvialis. In one embodiment, Astaxanthin is from an extract of Euphausia pacifica. In one embodiment, Astaxanthin is from an extract of Euphausia superba. In one embodiment, Astaxanthin is from an extract of Pandalus borealis.

Studies have shown that Astaxanthin can improve cosmetic appearance of human skin. In one embodiment, Astaxanthin is an antioxidant. In one embodiment, Astaxanthin is in a topical treatment. In one embodiment, Astaxanthin is in an oral treatment. In one embodiment, Astaxanthin treats skin conditions. In one embodiment, Astaxanthin treats skin conditions in all layers of the corneocyte, epidermis, basal, or dermis layer.

In one embodiment, the compositions disclosed herein are in a powder.

As used herein, the term "powder" refers to dry, solid particles of matter. In one embodiment, the powder is composed of large particles. In one embodiment, the powder is composed of small particles. In one embodiment, the powder is composed of uniformly sized particles. In one embodiment, the powder is composed of non uniformly sized particles.

In one embodiment, the compositions disclosed herein are a gel.

As used herein, the term "gel" refers to a semi-rigid colloidal dispersion of a solid with a liquid or gas, jelly, glue, etc. In one embodiment, the gel is composed of an extract. In one embodiment, the gel comprises an emulsifier. In one embodiment, the gel comprises a solvent, e.g., an alcohol.

In one embodiment, the compositions disclosed herein comprise synthetic compounds.

As used herein, the term "synthetic" refers to an engineered compound or compounds through a process or series of processes, often performed in a laboratory. In one embodiment, the compositions disclosed herein are made in a laboratory. In one embodiment, the compositions herein are made from natural extracts. In one embodiment, the compositions disclosed herein are made entirely from synthetic compounds.

As used herein, the term "Polypodium Leucotomos extract" refers to a composition made from the plant material of the Polypodium Leucotomos plant. The Polypodium Leucotomos plant is also referred to as Phlebodium aureum, aka, golden polypody, golden serpent fern, cabbage palm fern, gold-foot fern, or hare-foot fern. Polypodium Leucotomos extract is also referred to as fern extract. In one embodiment, the Polypodium Leucotomos extract is made by extracting cultivated plant material with a solvent, such as an alcohol, e.g., ethanol, and then removing the solvent. In one embodiment, once separated from the insoluble plant materials the extract is a liquid. The liquid can be removed, e.g. through evaporation or distillation, to produce a solid extract. In one embodiment, the Polypodium Leucotomos extract is purified. In one embodiment, the Polypodium Leucotomos extract is a formulation made from synthetic compounds. In one embodiment, the Polypodium Leucotomos extract is a formulation made from other extracts of plant material.

In one embodiment, the extract of Polypodium Leucotomos contains 10 times the concentration of phytochemicals, naturally occurring plant chemical compounds, compared to the dried cultivated plant material.

In one embodiment, the extract of Polypodium Leucotomos contains between 10-100 times the concentration of phytochemicals compared to the dried cultivated plant material.

In one embodiment, the extract of Polypodium Leucotomos contains 100-500 times the concentration of phytochemicals compared to the dried cultivated plant material.

In one embodiment, the extract of Polypodium Leucotomos contains 500-1,000 times the concentration of phytochemicals compared to the dried cultivated plant material.

In one embodiment, the extract of Polypodium Leucotomos extract refers to a mixture of one or more of the following compounds: 4-hydroxycinnamic acid, 3 methoxy-4-hydroxycinnamic acid, 3,4-dihydroxycinnamic acid, 3-methoxy-4-hydroxybenzoic acid, or 3-caffeoilquinic acid.

As used herein, the term "4-hydroxycinnamic acid" (p-coumaric acid) refers to a compound with the following structural formula:

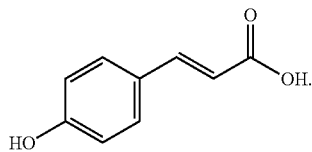

In one embodiment, p-coumaric acid refers to an isomer of coumaric acid with the hydroxyl group in the para position. However, within the context of this disclosure the term "p-coumaric acid" may also refer to the other isomers in which the hydroxyl group is in the meta position, ortho position, or any combination of all three isomers.

As used herein, the term "3 methoxy-4-hydroxycinnamic acid" (ferulic acid) refers to a compound with the following structural formula:

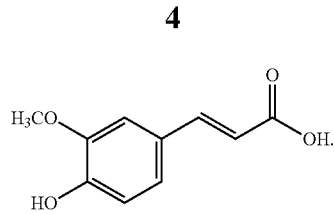

In one embodiment, ferulic acid is from the extract of pine bark. In one embodiment, ferulic acid is derived from wheat bran. In one embodiment, ferulic acid inhibits UVA-induced matrix metalloproteinase-1 through regulation of antioxidant defense system in keratinocyte HaCaT cells.

As used herein, the term "3,4-dihydroxycinnamic acid" (caffeic acid) refers to a compound with the following structural formula:

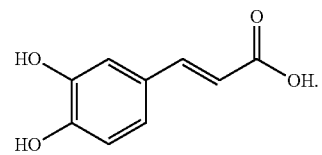 [SMILES: O=C(O)/C=C/c1ccc(O)c(O)c1]

In one embodiment, caffeic acid is a yellow solid. In one embodiment, caffeic acid is derived from Eucalyptus globulus. In one embodiment, caffeic acid inhibits UVA-induced matrix metalloproteinase-1 through regulation of antioxidant defense system in keratinocyte HaCaT cells.

As used herein, the term "3-methoxy-4-hydroxybenzoic acid" (vanillic acid) refers to a compound with the following structural formula:

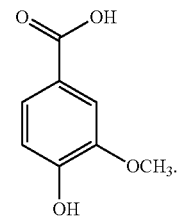 [SMILES: COc1cc(C(=O)O)ccc1O]

In one embodiment, vanillic acid is a flavoring agent. In one embodiment, vanillic acid is derived from oxidizing vanillin. In one embodiment, vanillic acid is derived from Angelica sinensis.

As used herein, the term "3-caffeoilquinic acid" (chlorogenic acid) refers to a compound with the following structural formula:

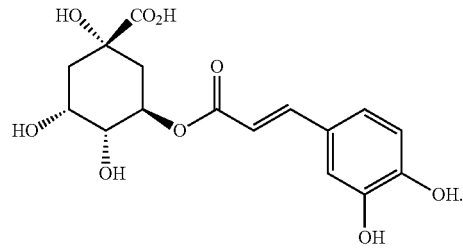 [SMILES: O=C(/C=C/c1ccc(O)c(O)c1)O[C@@H]1C[C@](O)(C(=O)O)C[C@@H](O)[C@H]1O]

In one embodiment, chlorogenic acid is derived from Phyllostachys edulis. In one embodiment, chlorogenic acid is an anti-inflammatory.

In one embodiment, the compositions disclosed herein comprise Astaxanthin, Polypodium Leucotomos extract, and hyaluronic acid.

As used herein, the term "hyaluronic acid" refers to a compound with the following structural formula:

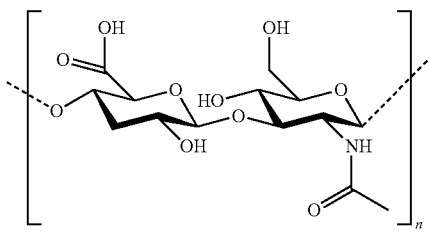

In one embodiment, n is an integer from 1 to infinity. In one embodiment, hyaluronic acid is an inflammatory. In one embodiment, hyaluronic acid regulates inflammation of skin. In one embodiment, hyaluronic acid regulates cell migration. In one embodiment, hyaluronic acid manipulates keratinocyte proliferation.

In one embodiment, the composition disclosed herein comprises Astaxanthin, Polypodium Leucotomos extract, and Cat's Claw extract.

In one embodiment, the composition disclosed herein comprises Astaxanthin, Polypodium Leucotomos extract, Hyaluronic acid, and Cat's Claw extract.

As used herein, the term "Cat's Claw extract" refers to a mixture composed of compounds from the plant *Uncaria tomentosa* or *Uncaria guianensis*. In one embodiment, Cat's Claw extract comprises alkaloids.

As used herein the term "alkaloid" refer to a group of naturally occurring compounds that mostly contain basic nitrogen atoms. In some instances, alkaloids can have some related compounds with neutral and even weakly acidic properties.

In one embodiment, Cat's Claw extract comprises polyphenols.

As used herein, the term "polyphenol" refer to a structural class of chemical compounds characterized by the presence of multiple phenol structural units. Often, the number and characteristics of these phenolic structures underlie the physical, chemical, and biological properties of particular members of the class.

In one embodiment, the composition disclosed herein comprises Astaxanthin, Polypodium Leucotomos extract, and Collagen type II.

As used herein, the term "Collagen type II" refers to a peptide and component of joint cartilage. Collagen is one of the main structural protein in the extracellular space in various connective tissues in animal bodies.

In one embodiment, the composition disclosed herein comprises Astaxanthin, Polypodium Leucotomos extract, and Hesperidin.

As used herein, the term "Hesperidin" refers to a compound of the following structural formula:

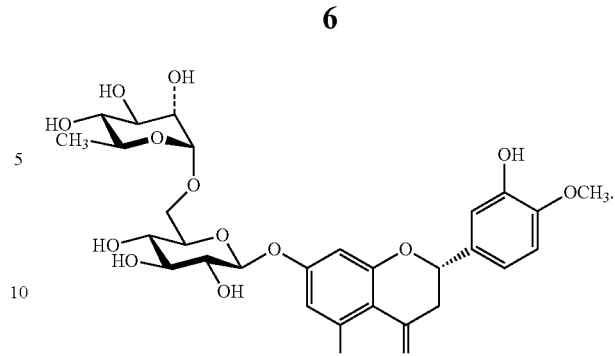

In one embodiment, Hesperidin is from the extract of citrus fruits, e.g., oranges, limes, lemons, etc. In one embodiment, Hesperidin regulates the production of tyrosinase.

In one embodiment, the composition disclosed herein comprises Astaxanthin, Polypodium Leucotomos extract, and Horse tail extract.

As used herein, the term "Horse tail extract" refers to a mixture of compounds from a family of vascular plants that reproduce by spores rather than seeds. Horse tail is unique for having about 25% of its dry weight composed of silica. In one embodiment, Horse tail comprises campesterol. In one embodiment, Horse tail comprises palustrine. In one embodiment, Horse tail comprises equisetrin. In one embodiment, Horse tail comprises equisetonin.

As used herein, the term "campesterol" refers to a compound of the following structure:

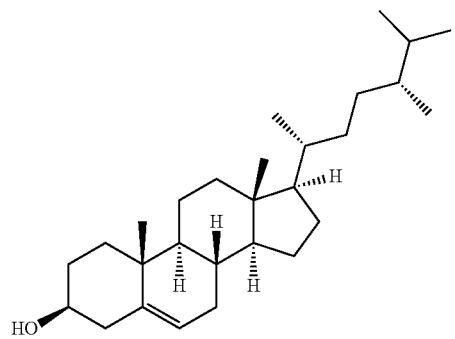

In one embodiment, campesterol is an anti-inflammatory. In one embodiment, campesterol is derived from Brassica campestris.

As used herein, the term "palustrine" refers to a compound with the following structural formula:

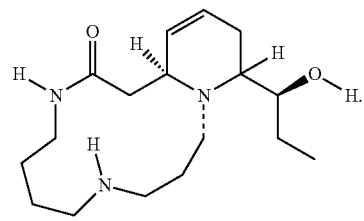

In one embodiment, palustrine is derived from Horse tail.

As used herein, the term "equisetrin" refers to a compound with the following structural formula:

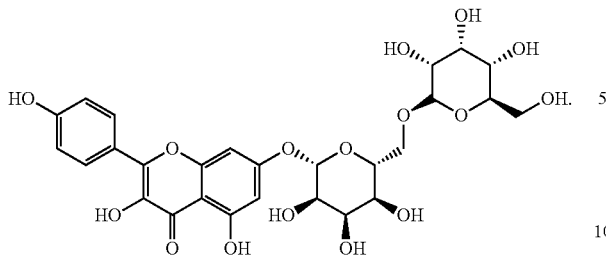

In one embodiment, equisetrin is derived from Horse tail.

As used herein, the term "equisetonin" refers to a compound with the following structural formula:

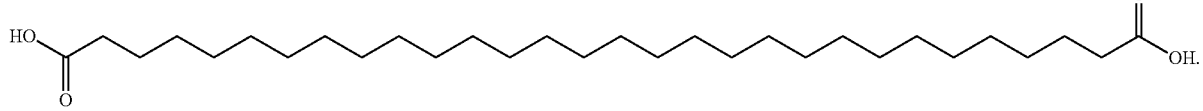

In one embodiment, equisetonin is a diuretic.

In one embodiment, the composition comprises Astaxanthin, Polypodium Leucotomos extract, and biotin.

As used herein, the term "biotin" refers to a compound with the following structural formula, its salt, and/or derivative forms:

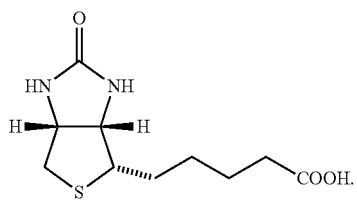 [SMILES: O=C(O)CCCC[C@@H]1SC[C@@H]2NC(=O)N[C@@H]21]

In one embodiment, biotin regulates keratin structure. In one embodiment, biotin regulates metabolism in mammals.

In one embodiment, the composition comprises Astaxanthin, Polypodium Leucotomos extract, and Vitamin C.

As used herein, the term "Vitamin C" refers to a compound of the following structural formula, or its salt, derivative forms and/or ascorbic acid:

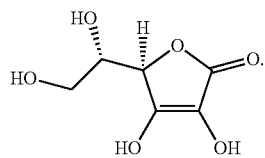

In one embodiment, Vitamin C is a cofactor for the synthesis of collagen. In one embodiment, Vitamin C is an antioxidant.

In one embodiment the composition comprises Astaxanthin, Polypodium Leucotomos extract, and Vitamin E.

As used herein, the term "Vitamin E" refers to a compound of the following structural formula and/or derivatives thereof:

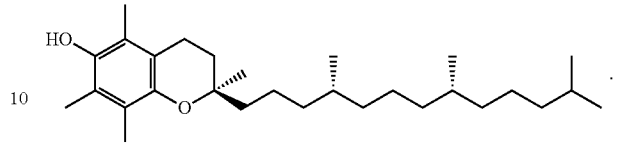

In one embodiment, Vitamin E refers to D-alpha Tocopherol Acetate with the following structural formula:

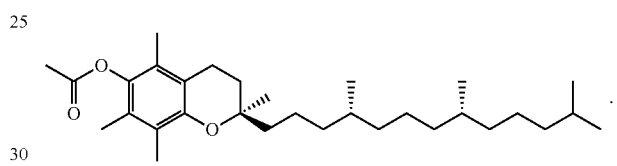

In one embodiment, the composition disclosed herein comprises about 0.5 mg to 80 mg of Astaxanthin.

In one embodiment, the composition disclosed herein comprises about 0.5 mg to 20 g of Polypodium Leucotomos extract.

In one embodiment, the composition disclosed herein comprises about 0.5 mg to 20 g of Cat's Claw extract.

In one embodiment, the composition disclosed herein comprises about 0.5 mg to 60 g of Hyaluronic acid.

In one embodiment, the composition disclosed herein comprises:
0.5 mg to 80 mg of Astaxanthin;
0.5 mg to 20 g of Polypodium Leucotomos extract;
0.5 mg to 20 g of Cat's Claw extract; and
0.5 mg to about 60 g of Hyaluronic acid.

In one embodiment, the mass ratio of Polypodium Leucotomos extract: Astaxanthin is about 200,000:1 to about 100,000:1.

As used herein, the term "mass ratio" refers to the amount of one compound in relation to another compound or compounds.

In one embodiment, the mass ratio of Polypodium Leucotomos extract:Astaxanthin is about 100,000:1 to about 50,000:1.

In one embodiment, the mass ratio of Polypodium Leucotomos extract:Astaxanthin is about 50,000:1 to about 10,000:1.

In one embodiment, the mass ratio of Polypodium Leucotomos extract:Astaxanthin is about 10,000:1 to about 5,000:1.

In one embodiment, the mass ratio of Polypodium Leucotomos extract:Astaxanthin is about 5,000:1 to about 1,000:1.

In one embodiment, the mass ratio of Polypodium Leucotomos extract:Astaxanthin is about 1,000:1 to about 100:1.

In one embodiment, the mass ratio of Polypodium Leucotomos extract:Astaxanthin is about 100:1 to about 10:1.

In one embodiment, the mass ratio of Polypodium Leucotomos extract:Astaxanthin is about 10:1 to 5:1.

In one embodiment, the mass ratio of Polypodium Leucotomos extract:Astaxanthin is about 5:1 to 1:1.

In one embodiment, the mass ratio of Polypodium Leucotomos extract:Astaxanthin is about 1:1 to about 1:2.

In one embodiment, the mass ratio of Polypodium Leucotomos extract:Astaxanthin is about 1:2 to about 1:10.

In one embodiment, the mass ratio of Polypodium Leucotomos extract:Astaxanthin is about 1:10 to about 1:20.

In one embodiment, the mass ratio of Polypodium Leucotomos extract:Astaxanthin is about 1:20 to about 1:40.

In one embodiment, the mass ratio of Polypodium Leucotomos extract:Astaxanthin is about 1:40 to about 1:80.

In one embodiment, the mass ratio of Polypodium Leucotomos extract:Astaxanthin is about 1:80 to about 1:160.

Disclosed herein is a composition comprising Astaxanthin and Cat's Claw Extract.

In one embodiment, the mass ratio of Astaxanthin:Cat's Claw Extract is about 1:200,000 to about 1:100,000.

In one embodiment, the mass ratio of Astaxanthin:Cat's Claw Extract is about 1:100,000 to about 1:50,000.

In one embodiment, the mass ratio of Astaxanthin:Cat's Claw Extract is about 1:50,000 to about 1:10,000.

In one embodiment, the mass ratio of Astaxanthin:Cat's Claw Extract is about 1:10,000 to about 1:5,000.

In one embodiment, the mass ratio of Astaxanthin:Cat's Claw Extract is about 1:5,000 to about 1:1,000.

In one embodiment, the mass ratio of Astaxanthin:Cat's Claw Extract is about 1:1,000 to about 1:100.

In one embodiment, the mass ratio of Astaxanthin:Cat's Claw Extract is about 1:100 to about 1:10.

In one embodiment, the mass ratio of Astaxanthin:Cat's Claw Extract is about 1:10 to about 1:5.

In one embodiment, the mass ratio of Astaxanthin:Cat's Claw Extract is about 1:5 to about 1:1.

In one embodiment, the mass ratio of Astaxanthin:Cat's Claw Extract is about 1:1 to about 2:1.

In one embodiment, the mass ratio of Astaxanthin:Cat's Claw Extract is about 2:1 to about 10:1.

In one embodiment, the mass ratio of Astaxanthin:Cat's Claw Extract is about 10:1 to about 20:1.

In one embodiment, the mass ratio of Astaxanthin:Cat's Claw Extract is about 40:1 to about 80:1.

In one embodiment, the mass ratio of Astaxanthin:Cat's Claw Extract is about 80:1 to about 160:1.

Disclosed herein is a composition comprising Astaxanthin and Hyaluronic acid.

In one embodiment, the mass ratio of Astaxanthin:Hyaluronic acid is about 1:600,000 to about 1:300,000.

In one embodiment, the mass ratio of Astaxanthin:Hyaluronic acid is about 1:300,000 to about 1:150,000.

In one embodiment, the mass ratio of Astaxanthin:Hyaluronic acid is about 1:150,000 to about 1:100,000.

In one embodiment, the mass ratio of Astaxanthin:Hyaluronic acid is about 1:100,000 to about 1:50,000.

In one embodiment, the mass ratio of Astaxanthin:Hyaluronic acid is about 1:50,000 to about 10,000.

In one embodiment, the mass ratio of Astaxanthin:Hyaluronic acid is about 1:10,000 to about 1:1,000.

In one embodiment, the mass ratio of Astaxanthin:Hyaluronic acid is about 1:1,000 to about 1:100.

In one embodiment, the mass ratio of Astaxanthin:Hyaluronic acid is about 1:100 to about 1:10.

In one embodiment, the mass ratio of Astaxanthin:Hyaluronic acid is about 1:10 to about 1:5.

In one embodiment, the mass ratio of Astaxanthin:Hyaluronic acid is about 1:5 to about 1:1.

In one embodiment, the mass ratio of Astaxanthin:Hyaluronic acid is about 1:1 to about 2:1.

In one embodiment, the mass ratio of Astaxanthin:Hyaluronic acid is about 2:1 to about 10:1.

In one embodiment, the mass ratio of Astaxanthin:Hyaluronic acid is about 10:1 to about 20:1.

In one embodiment, the mass ratio of Astaxanthin:Hyaluronic acid is about 20:1 to about 40:1.

In one embodiment, the mass ratio of Astaxanthin:Hyaluronic acid is about 40:1 to about 80:1.

In one embodiment, the mass ratio of Astaxanthin:Hyaluronic acid is about 80:1 to about 160:1.

Disclosed herein is a composition comprising Cat's Claw extract and Polypodium Leucotomos extract.

In one embodiment, comprises Cat's Claw extract, Polypodium Leucotomos, and Hyaluronic Acid.

In one embodiment, comprises Cat's Claw extract, Polypodium Leucotomos, and Collagen type II.

In one embodiment, comprises Cat's Claw extract, Polypodium Leucotomos, and Hesperidin.

In one embodiment, comprises Cat's Claw extract, Polypodium Leucotomos, and Horse tail extract.

In one embodiment, comprises Cat's Claw extract, Polypodium Leucotomos, and biotin.

In one embodiment, comprises Cat's Claw extract, Polypodium Leucotomos, and Vitamin C.

In one embodiment, the compositions disclosed herein comprise Cat's Claw extract, Polypodium Leucotomos, and Vitamin E.

In one embodiment, the compositions disclosed herein comprise Cat's Claw extract, Polypodium Leucotomos, and Pine bark extract.

Disclosed herein is a composition comprising Cat's Claw and Astaxanthin.

In one embodiment, the composition disclosed herein comprise Cat's Claw, Astaxanthin, and Hyaluronic Acid.

In one embodiment, the composition disclosed herein comprise Cat's Claw, Astaxanthin, and Collagen type II.

In one embodiment, the composition disclosed herein comprise Cat's Claw, Astaxanthin, and Hesperidin.

In one embodiment, the composition disclosed herein comprise Cat's Claw, Astaxanthin, and Horse tail.

In one embodiment, the composition disclosed herein comprise Cat's Claw, Astaxanthin, and biotin.

In one embodiment, the composition disclosed herein comprise Cat's Claw, Astaxanthin, and Vitamin C.

In one embodiment, the composition disclosed herein comprise Cat's Claw, Astaxanthin, and Vitamin E.

In one embodiment, the composition disclosed herein comprise Cat's Claw, Astaxanthin, and Pine bark extract.

Disclosed herein is a method of protecting the skin, comprising administering a composition of Polypodium Leucotomos extract, and Astaxanthin.

As used herein, the term "administering" refers to providing, issuing, and/or applying the compositions disclosed herein. Examples include, but are not limited to, an oral application, a pill, a liquid extract, a topical cream, and/or a tincture.

Disclosed herein is a method of treating or preventing the occurrence of skin cancer, comprising administering a composition of Polypodium Leucotomos extract and Astaxanthin. In one embodiment, the composition comprises Hyaluronic Acid, Cat's Claw extract, Collagen type II, Hesperidin, Horse tail extract, Pine bark extract, biotin, Vitamin C, or Vitamin E.

As used herein the term "skin cancer" refers to the mutation or damage of the DNA in skin cells that can result in abnormal cell growth, moles, tumors, and/or melanoma. One cause of skin cancer is exposure to radiation, such as UV radiation. For example, UV radiation from the sun. UV radiation has three types: UVA, UVB, and UVC. UVA rays, wavelength of 315-400 nm, can damage skin cells and skin cell DNA. UVA rays often create long term skin damage like wrinkles and cancer. UVB rays, wavelength of 280-315 nm, can damage skin cell DNA as well and can cause sunburn. UVC rays, wavelength of 100-280 nm, does not often go past the Earth's atmosphere and rarely causes skin damage.

Disclosed herein is a method of treating or preventing skin damage from UV radiation, comprising administering a composition of Polypodium Leucotomos extract and Astaxanthin. In one embodiment, the composition comprises Hyaluronic Acid, Cat's Claw extract, Collagen type II, Hesperidin, Horse tail extract, Pine bark extract, biotin, Vitamin C, or Vitamin E.

As used herein, the term "skin damage" refers to a number of conditions as a result of exposure to the sun, radiation, compounds, etc., that include medical and cosmetic changes to the skin. Examples include, but are not limited to, redness, irritation, pain, discoloration, blisters, wrinkles, skin elasticity, cancer, inflammation, skin hydration, etc.

Disclosed herein is a method of increasing DNA repair in skin, comprising administering a composition of Polypodium Leucotomos extract and Astaxanthin. In one embodiment, the composition comprises Hyaluronic Acid, Cat's Claw extract, Collagen type II, Hesperidin, Horse tail extract, Pine bark extract, biotin, Vitamin C, or Vitamin E.

As used herein, the term "DNA repair" refers to a process or processes by which a cell identifies and corrects damage to the DNA molecules, e.g. DNA in skin cells. Radiation, e.g. UV radiation from the sun, can cause DNA damage, resulting in as many as 1 million individual molecular lesions per cell per day. Many of these lesions cause structural damage to the DNA molecule and can alter or eliminate the cell's ability to transcribe the gene that the affected DNA encodes. Other lesions induce potentially harmful mutations in the cell's genome, which affect the survival of its daughter cells after it undergoes mitosis. As a consequence, the DNA repair process is constantly active as it responds to damage in the DNA structure.

Disclosed herein is a method of reducing inflammation in the skin, comprising administering a composition of Polypodium Leucotomos extract and Astaxanthin. In one embodiment, the composition comprises Hyaluronic Acid, Cat's Claw extract, Collagen type II, Hesperidin, Horse tail extract, Pine bark extract, biotin, Vitamin C, or Vitamin E.

As used herein, the term "inflammation of the skin" refers to the body's immune response to remove harmful stimuli on the skin. Inflammation often occurs when the skin is reddened, swollen, hot, and/or painful as a result of injury or infection. One cause of inflammation can be overexposure to the sun. Inflammation can also cause more inflammation.

Disclosed herein is a method of decreasing wrinkles, comprising administering a composition of Polypodium Leucotomos extract and Astaxanthin. In one embodiment, the composition comprises Hyaluronic Acid, Cat's Claw extract, Collagen type II, Hesperidin, Horse tail extract, Pine bark extract, biotin, Vitamin C, or Vitamin E.

As used herein, the term "wrinkle" refers to a line, fold, crease, or ridge in the skin. Wrinkles are caused by aging, exposure to sun, lack of sleep, lack of water, and smoking. Wrinkles can be divided into two groups: fine surface lines and deep furrows related to muscle contraction.

Disclosed herein is a method of increasing skin hydration, comprising administering a composition of Polypodium Leucotomos extract and Astaxanthin. In one embodiment, the composition comprises Hyaluronic Acid, Cat's Claw extract, Collagen type II, Hesperidin, Horse tail extract, Pine bark extract, biotin, Vitamin C, or Vitamin E.

As used herein the term "skin hydration" refers to the skin's ability to hold onto moisture. Skin naturally produces oil (sebum) that helps the skin retain moisture. However, everyday activities cause the skin to lose its natural moisture, e.g., sun exposure. Dry skin can lead to irritation and can be difficult to get rid of, which can also lead to skin damage.

Disclosed herein is a method of increasing skin elasticity, comprising administering a composition of Polypodium Leucotomos extract and Astaxanthin. In one embodiment, the composition comprises Hyaluronic Acid, Cat's Claw extract, Collagen type II, Hesperidin, Horse tail extract, Pine bark extract, biotin, Vitamin C, or Vitamin E.

As used herein the term "skin elasticity" refers to the skin's ability to stretch and retract to its previous state. One known cause of the breakdown of skin elasticity is free radical destruction. Free radical destruction contributes to a decrease in the production of collagen and elastin which are key factors in skin elasticity. While a condition as a result of aging, skin elasticity can be affected by a number things including genetics, physical activity, and sun exposure.

Disclosed herein is a method of increasing antioxidants in the skin, comprising administering a composition of Polypodium Leucotomos extract and Astaxanthin. In one embodiment, the composition comprises Hyaluronic Acid, Cat's Claw extract, Collagen type II, Hesperidin, Horse tail extract, Pine bark extract, biotin, Vitamin C, or Vitamin E.

As used herein, the term "antioxidant" refers to a substance that inhibits oxidation. Oxidation is the loss of electrons or an increase in oxidative state aka oxidation number. Antioxidants help regulate free radicals which left unchecked free radicals can cause cell damage that can lead to a number of health problems including cancer, heart disease, decline in brain function, and skin damage.

Disclosed herein is a method of increasing the time to an erythema dose, comprising administering a composition of Polypodium Leucotomos extract and Astaxanthin. In one embodiment, the composition comprises Hyaluronic Acid, Cat's Claw extract, Collagen type II, Hesperidin, Horse tail extract, Pine bark extract, biotin, Vitamin C, or Vitamin E.

As used herein the term "increasing time to an erythema dose" refers to increasing the amount of exposure to radiation until reddening of the skin occurs. This reddening is often the result of a sunburn. The radiation can be from x-rays or UV radiation.

Disclosed herein is a method of reducing the occurrence of sunburns, comprising administering a composition of Polypodium Leucotomos extract and Astaxanthin. In one embodiment, the composition comprises Hyaluronic Acid, Cat's Claw extract, Collagen type II, Hesperidin, Horse tail extract, Pine bark extract, biotin, Vitamin C, or Vitamin E.

As used herein, the term "sunburn" refers to a radiation burn of the skin after exposure to the radiation. For example, UV radiation from the sun or tanning lamps. Common symptoms include reddening of the skin, pain to the touch, fatigue, inflammation, and dizziness. The radiation may also cause DNA damage, which may, in turn, trigger several defense mechanisms of the body including melanin production, DNA repair and peeling of the skin.

EXAMPLES

The following examples are for illustrative purposes and are non-limiting.

Example 1

20 mg Polypodium leucotomos extract, 1 mg Hyaluronic acid, 15 mg Cat's Claw extract, and 1 mg of Astaxanthin was weighed. The compounds were combined in a container and was mixed to make a homogenous mixture.

5 mg Collagen Type II, 5 mg Hesperidin, and 5 mg of Horse tail was weighed. These compounds were then combined to make a second homogenous mixture in a separate container.

30 mg of Vitamin C, 10 IU of Vitamin E, and 150 mcg of Biotin was weighed. These compounds were mixed together to make a third homogenous mixture in a separate container.

All three homogeneous mixtures were combined to make one single homogeneous mixture.

Example 2

20 mg Polypodium leucotomos extract, 1 mg Hyaluronic acid, 15 mg Cat's Claw extract, and 1 mg of Astaxanthin was weighed. The compounds were combined in a container and was mixed to make a homogenous mixture.

30 mg of Vitamin C, 10 IU of Vitamin E, and 150 mcg of Biotin was weighed. These compounds were mixed together to make a second homogenous mixture in a separate container.

Both homogeneous mixtures were combined to make one single homogeneous mixture.

Example 3

1,000 mg Polypodium leucotomos extract, 10 mg Hyaluronic acid, 60 mg Cat's Claw extract, and 4 mg of Astaxanthin was weighed. The compounds were combined in a container and was mixed to make a homogenous mixture.

60 mg Collagen Type II, 10 mg Hesperidin, and 10 mg of Horse tail was weighed. These compounds were then combined to make a second homogenous mixture in a separate container.

30 mg of Vitamin C, 10 IU of Vitamin E, and 150 mcg of Biotin was weighed. These compounds were mixed together to make a third homogenous mixture in a separate container.

All three homogeneous mixtures were combined to make one single homogeneous mixture.

Example 4

1,000 mg Polypodium leucotomos extract, 10 mg Hyaluronic acid, 60 mg Cat's Claw extract, and 4 mg of Astaxanthin was weighed. The compounds were combined in a container and was mixed to make a homogenous mixture.

30 mg of Vitamin C, 10 IU of Vitamin E, and 150 mcg of Biotin was weighed. These compounds were mixed together to make a second homogenous mixture in a separate container.

Both homogeneous mixtures were combined to make one single homogeneous mixture.

Example 5

480 mg Polypodium leucotomos extract, 100 mg Hyaluronic acid, 300 mg Cat's Claw extract, and 40 mg of Astaxanthin was weighed. The compounds were combined in a container and was mixed to make a homogenous mixture.

60 mg Collagen Type II, 50 mg Hesperidin, and 50 mg of Horse tail was weighed. These compounds were then combined to make a second homogenous mixture in a separate container.

30 mg of Vitamin C, 10 IU of Vitamin E, and 2 mcg of Biotin was weighed. These compounds were mixed together to make a third homogenous mixture in a separate container.

All three homogeneous mixtures were combined to make one single homogeneous mixture.

Example 6

480 mg Polypodium leucotomos extract, 100 mg Hyaluronic acid, 300 mg Cat's Claw extract, and 40 mg of Astaxanthin was weighed. The compounds were combined in a container and was mixed to make a homogenous mixture.

30 mg of Vitamin C, 10 IU of Vitamin E, and 2 mcg of Biotin was weighed. These compounds were mixed together to make a second homogenous mixture in a separate container.

Both homogeneous mixtures were combined to make one single homogeneous mixture.

Example 7

50 mg Polypodium leucotomos extract, 10 mg Hyaluronic acid, 1,000 mg Cat's Claw extract, and 1 mg of Astaxanthin was weighed. The compounds were combined in a container and was mixed to make a homogenous mixture.

60 mg Collagen Type II, 10 mg Hesperidin, and 20 mg of Horse tail was weighed. These compounds were then combined to make a second homogenous mixture in a separate container.

60 mg of Vitamin C, 30 IU of Vitamin E, and 1 mcg of Biotin was weighed. These compounds were mixed together to make a third homogenous mixture in a separate container.

All three homogeneous mixtures were combined to make one single homogeneous mixture.

Example 8

50 mg Polypodium leucotomos extract, 10 mg Hyaluronic acid, 1,000 mg Cat's Claw extract, and 1 mg of Astaxanthin was weighed. The compounds were combined in a container and was mixed to make a homogenous mixture.

60 mg of Vitamin C, 40 IU of Vitamin E, and 1 mcg of Biotin was weighed. These compounds were mixed together to make a second homogenous mixture in a separate container.

Both homogeneous mixtures were combined to make one single homogeneous mixture.

Example 9

500 mg Polypodium leucotomos extract, 1 mg Hyaluronic acid, 500 mg Cat's Claw extract, and 4 mg of Astaxanthin was weighed. The compounds were combined in a container and was mixed to make a homogenous mixture.

200 mg Collagen Type II, 30 mg Hesperidin, and 30 mg of Horse tail was weighed. These compounds were then combined to make a second homogenous mixture in a separate container.

30 mg of Vitamin C, 10 IU of Vitamin E, and 2000 mcg of Biotin was weighed. These compounds were mixed together to make a third homogenous mixture in a separate container.

All three homogeneous mixtures were combined to make one single homogeneous mixture.

Example 10

500 mg Polypodium leucotomos extract, 1 mg Hyaluronic acid, 500 mg Cat's Claw extract, and 4 mg of Astaxanthin was weighed. The compounds were combined in a container and was mixed to make a homogenous mixture.

30 mg of Vitamin C, 10 IU of Vitamin E, and 200 mcg of Biotin was weighed. These compounds were mixed together to make a second homogenous mixture in a separate container.

Both homogeneous mixtures were combined to make one single homogeneous mixture.

Example 11

220 mg Polypodium leucotomos extract, 1 mg Hyaluronic acid, 600 mg Cat's Claw extract, and 6 mg of Astaxanthin was weighed. The compounds were combined in a container and was mixed to make a homogenous mixture.

60 mg Collagen Type II, 100 mg Hesperidin, and 50 mg of Horse tail was weighed. These compounds were then combined to make a second homogenous mixture in a separate container.

30 mg of Vitamin C, 20 IU of Vitamin E, and 1 mg of Biotin was weighed. These compounds were mixed together to make a third homogenous mixture in a separate container.

All three homogeneous mixtures were combined to make one single homogeneous mixture.

Example 12

220 mg Polypodium leucotomos extract, 1 mg Hyaluronic acid, 600 mg Cat's Claw extract, and 6 mg of Astaxanthin was weighed. The compounds were combined in a container and was mixed to make a homogenous mixture.

30 mg of Vitamin C, 20 IU of Vitamin E, and 1 mg of Biotin was weighed. These compounds were mixed together to make a third homogenous mixture in a separate container.

All three homogeneous mixtures were combined to make one single homogeneous mixture.

Example 13

180 mg Polypodium leucotomos extract, 800 mg Hyaluronic acid, 60 mg Cat's Claw extract, and 4 mg of Astaxanthin was weighed. The compounds were combined in a container and was mixed to make a homogenous mixture.

30 mg Collagen Type II, 10 mg Hesperidin, and 10 mg of Horse tail was weighed. These compounds were then combined to make a second homogenous mixture in a separate container.

20 mg of Vitamin C, 5 IU of Vitamin E, and 200 mcg of Biotin was weighed. These compounds were mixed together to make a third homogenous mixture in a separate container.

All three homogeneous mixtures were combined to make one single homogeneous mixture.

Example 14

180 mg Polypodium leucotomos extract, 800 mg Hyaluronic acid, 60 mg Cat's Claw extract, and 4 mg of Astaxanthin was weighed. The compounds were combined in a container and was mixed to make a homogenous mixture.

20 mg of Vitamin C, 5 IU of Vitamin E, and 200 mcg of Biotin was weighed. These compounds were mixed together to make a second homogenous mixture in a separate container.

Both homogeneous mixtures were combined to make one single homogeneous mixture.

Example 15

20 mg Polypodium leucotomos extract, 900 mg Hyaluronic acid, 15 mg Cat's Claw extract, and 1 mg of Astaxanthin was weighed. The compounds were combined in a container and was mixed to make a homogenous mixture.

100 mg Collagen Type II, 20 mg Hesperidin, and 15 mg of Horse tail was weighed. These compounds were then combined to make a second homogenous mixture in a separate container.

40 mg of Vitamin C, 15 IU of Vitamin E, and 300 mcg of Biotin was weighed. These compounds were mixed together to make a third homogenous mixture in a separate container.

All three homogeneous mixtures were combined to make one single homogeneous mixture.

Example 16

20 mg Polypodium leucotomos extract, 900 mg Hyaluronic acid, 15 mg Cat's Claw extract, and 1 mg of Astaxanthin was weighed. The compounds were combined in a container and was mixed to make a homogenous mixture.

40 mg of Vitamin C, 15 IU of Vitamin E, and 300 mcg of Biotin was weighed. These compounds were mixed together to make a second homogenous mixture in a separate container.

Both homogeneous mixtures were combined to make one single homogeneous mixture.

Example 17

240 mg Polypodium leucotomos extract, 100 mg Hyaluronic acid, 150 mg Pine Bark extract, and 4 mg of Astaxanthin was weighed. The compounds were combined in a container and was mixed to make a homogenous mixture.

60 mg Collagen Type II, 25 mg Hesperidin, and 20 mg of Horse tail was weighed. These compounds were then combined to make a second homogenous mixture in a separate container.

250 mg of Vitamin C, 50 IU of Vitamin E, and 2 mg of Biotin was weighed. These compounds were mixed together to make a third homogenous mixture in a separate container.

All three homogeneous mixtures were combined to make one single homogeneous mixture.

Example 18

240 mg Polypodium leucotomos extract, 100 mg Hyaluronic acid, 150 mg Pine Bark extract, and 4 mg of Astaxanthin was weighed. The compounds were combined in a container and was mixed to make a homogenous mixture.

250 mg of Vitamin C, 50 IU of Vitamin E, and 2 mg of Biotin was weighed. These compounds were mixed together to make a second homogenous mixture in a separate container.

Both homogeneous mixtures were combined to make one single homogeneous mixture.

Although the present invention herein has been described with reference to various exemplary embodiments, it is to be understood that these embodiments are merely illustrative of the principles and applications of the present invention. Those having skill in the art would recognize that various modifications to the exemplary embodiments may be made, without departing from the scope of the invention.

Moreover, it should be understood that various features and/or characteristics of differing embodiments herein may be combined with one another. It is therefore to be understood that numerous modifications may be made to the illustrative embodiments and that other arrangements may be devised without departing from the scope of the invention. It is understood that any chemical structure or compound disclosed also includes any derivative or analogous forms, e.g., isomers (stereoisomers and structural isomerism), chirality, alpha, beta, gamma, etc.

Furthermore, other embodiments of the invention will be apparent to those skilled in the art from consideration of the specification and practice of the invention disclosed herein. It is intended that the specification and examples be considered as exemplary only, with a scope and spirit being indicated by the claims.

Finally, it is noted that, as used in this specification and the appended claims, the singular forms "a," "an," and "the," include plural referents unless expressly and unequivocally limited to one referent, and vice versa. As used herein, the term "include" or "comprising" and its grammatical variants are intended to be non-limiting, such that recitation of an item or items is not to the exclusion of other like items that can be substituted or added to the recited item(s).

I claim:

1. A composition for administering to a subject with skin cancer, skin damage, or inflammation comprising:
    Polypodium leucotomos extract;
    Hyaluronic acid;
    Astaxanthin; and
    a mixture of (a) Cat's claw extract, Collagen type II, Hesperidin, Horse tail extract, Vitamin C, Vitamin E, and biotin or (b) Pine bark extract, Collagen type II, Hesperidin, Horse tail extract, Vitamin C, Vitamin E, and biotin;
    wherein the mass ratio of Polypodium leucotomos extract: Astaxanthin is about 100:1 to about 10:1; and
    wherein the mass ratio of Astaxanthin:Hyaluronic acid is about 1:100 to about 1:10.

2. The composition of claim 1, wherein when the mixture is (a) and the mass ratio of Astaxanthin:Cat's claw extract is about 1:10 to about 1:5.

3. The composition of claim 1, wherein the mixture is (a) Cat's claw extract, Collagen type II, Hesperidin, Horse tail extract, Vitamin C, Vitamin E, and biotin.

4. The composition of claim 1, wherein the mixture is (b) Pine bark extract, Collagen type II, Hesperidin, Horse tail extract, Vitamin C, Vitamin E, and biotin.

5. The composition of claim 1, wherein the mass ratio of Polypodium leucotomos extract: Astaxanthin is about 85:1 to about 10:1.

6. The composition of claim 5, wherein the mass ratio of Polypodium leucotomos extract:Astaxanthin is about 65:1 to about 10:1.

7. The composition of claim 1, wherein the mass ratio of Astaxanthin:Hyaluronic acid is about 1:80 to about 1:10.

8. The composition of claim 7, wherein the mass ratio of Astaxanthin:Hyaluronic acid is about 1:60 to about 1:10.

9. The composition of claim 8, wherein the mass ratio of Astaxanthin:Hyaluronic acid is about 1:40 to about 1:10.

10. The composition of claim 9, wherein the mass ratio of Astaxanthin:Hyaluronic acid is about 1:30 to about 1:10.

11. The composition of claim 1, wherein the mass ratio of Astaxanthin:Hyaluronic acid is about 1:10 to about 1:5.

12. The composition of claim 1, wherein the mass ratio of Astaxanthin:Hyaluronic acid is about 1:5 to about 1:1.

13. The composition of claim 12, wherein the mass ratio of Astaxanthin:Hyaluronic acid is about 1:3 to about 1:1.

* * * * *